United States Patent
Ibsies

(10) Patent No.: US 10,254,852 B2
(45) Date of Patent: Apr. 9, 2019

(54) SPECIALIZED KEYBOARD FOR DENTAL EXAMINATIONS

(71) Applicant: Fadi Ibsies, Tigard, OR (US)

(72) Inventor: Fadi Ibsies, Tigard, OR (US)

(*) Notice: Subject to any disclaimer, the term of this patent is extended or adjusted under 35 U.S.C. 154(b) by 165 days.

(21) Appl. No.: 13/629,463

(22) Filed: Sep. 27, 2012

(65) Prior Publication Data

US 2014/0002364 A1    Jan. 2, 2014

Related U.S. Application Data

(63) Continuation-in-part of application No. 12/544,074, filed on Aug. 19, 2009, now abandoned.

(51) Int. Cl.

| | |
|---|---|
| *G06F 3/02* | (2006.01) |
| *G06F 19/00* | (2018.01) |
| *A61C 19/00* | (2006.01) |
| *G06F 1/16* | (2006.01) |
| *G06Q 50/24* | (2012.01) |
| *G16H 40/63* | (2018.01) |
| *G06F 3/00* | (2006.01) |

(52) U.S. Cl.
CPC ............ *G06F 3/0219* (2013.01); *A61C 19/00* (2013.01); *G16H 40/63* (2018.01); *G06F 1/1664* (2013.01); *G06F 19/30* (2013.01); *G06Q 50/24* (2013.01)

(58) Field of Classification Search
CPC .................................. G06F 19/30; G06Q 50/24
See application file for complete search history.

(56) References Cited

U.S. PATENT DOCUMENTS

| | | |
|---|---|---|
| D262,204 S | 12/1981 | Wilson et al. |
| D270,272 S | 8/1983 | Steele |
| 4,906,117 A | 3/1990 | Birdwell |
| 4,915,626 A | 4/1990 | Lemmey |
| 4,963,044 A | 10/1990 | Warner |
| 4,974,183 A | 11/1990 | Miller |
| 5,033,238 A | 7/1991 | Zubler |
| 5,084,833 A | 1/1992 | Matsuda et al. |

(Continued)

FOREIGN PATENT DOCUMENTS

| | | |
|---|---|---|
| EP | 1559390 | 1/2005 |
| EP | 1559390 | 8/2005 |

(Continued)

OTHER PUBLICATIONS

Clark Dental Support, "Florida Probe Support," at least as early as Jun. 29, 2015, web site, http://www.clarkdentalsupportco.uk/florida_probe_support.php, 2 pages.

(Continued)

*Primary Examiner* — Stella Higgs
(74) *Attorney, Agent, or Firm* — Law Office of Karen Dana Oster, LLC

(57) ABSTRACT

The present invention includes a device, system and method of use consisting of a specialized dental keyboard wherein the specialized keyboard resides as virtual keys on a touch screen panel on a device such as a tablet computer including such devices as an Apple iPad. The invention includes a software component that enables customer configurable keyboard layouts including a plurality of specialized keys that provide short-cut macros to streamline data entry during a dental exam.

31 Claims, 11 Drawing Sheets

(56) References Cited

U.S. PATENT DOCUMENTS

| | | |
|---|---|---|
| 5,235,510 A | 8/1993 | Yamada et al. |
| 5,303,148 A | 4/1994 | Mattson et al. |
| 5,562,448 A | 10/1996 | Mushabac |
| 5,584,588 A | 12/1996 | Harbaugh |
| 5,600,313 A | 2/1997 | Freedman |
| 5,742,700 A | 4/1998 | Yoon et al. |
| 5,752,827 A | 5/1998 | Baron et al. |
| 5,944,531 A | 8/1999 | Foley et al. |
| 6,010,260 A | 1/2000 | Chao |
| 6,227,850 B1 | 5/2001 | Chishti et al. |
| 6,241,406 B1 | 6/2001 | Yan |
| 6,295,052 B1 | 9/2001 | Kato et al. |
| 6,501,462 B1 | 12/2002 | Garner |
| 6,664,986 B1 | 12/2003 | Kopelman et al. |
| 7,010,153 B2 * | 3/2006 | Zimmermann ........ A61B 6/463 382/132 |
| D523,433 S | 6/2006 | O'Neil et al. |
| D533,875 S | 12/2006 | Miles et al. |
| D552,118 S | 10/2007 | Jung et al. |
| D565,046 S | 3/2008 | Ward |
| 7,343,305 B2 | 3/2008 | Benn et al. |
| D567,249 S | 4/2008 | Gunn et al. |
| 7,354,402 B2 | 4/2008 | Hoarau et al. |
| 7,369,116 B2 | 5/2008 | Logue |
| D573,989 S | 7/2008 | Ward |
| 7,454,705 B2 | 11/2008 | Cadez et al. |
| 7,478,327 B1 | 1/2009 | Reid |
| D590,836 S | 4/2009 | Schneider |
| D602,495 S | 10/2009 | Um et al. |
| D607,890 S | 1/2010 | Beavers et al. |
| D611,054 S | 3/2010 | Lin et al. |
| 7,689,317 B2 | 3/2010 | McGrady et al. |
| D614,644 S | 4/2010 | Kristensson et al. |
| D614,645 S | 4/2010 | Kristensson et al. |
| D617,336 S | 6/2010 | Beavers et al. |
| D617,337 S | 6/2010 | Beavers et al. |
| D619,608 S | 7/2010 | Meziere |
| D619,611 S | 7/2010 | Meziere |
| D621,410 S | 8/2010 | Verfuerth et al. |
| 7,819,598 B2 | 10/2010 | Griffin |
| D629,414 S | 12/2010 | Beavers et al. |
| D629,415 S | 12/2010 | Beavers et al. |
| D633,097 S | 2/2011 | Jewitt et al. |
| D638,852 S | 5/2011 | Skidmore et al. |
| D663,742 S | 7/2012 | Tanghe et al. |
| D664,549 S | 7/2012 | Gleasman et al. |
| D664,962 S | 8/2012 | Duggan et al. |
| D664,963 S | 8/2012 | Duggan et al. |
| D664,964 S | 8/2012 | Odell et al. |
| D665,394 S | 8/2012 | Duggan et al. |
| D675,218 S | 1/2013 | Arnold et al. |
| D679,722 S | 4/2013 | Ray |
| D682,293 S | 5/2013 | Kanalakis, Jr. et al. |
| D684,172 S | 6/2013 | Rytt et al. |
| D684,173 S | 6/2013 | Rytt et al. |
| D684,177 S | 6/2013 | Winther et al. |
| D684,588 S | 6/2013 | Gilani |
| D690,318 S | 9/2013 | Kluttz et al. |
| D690,723 S | 10/2013 | Steele et al. |
| 8,624,842 B2 | 1/2014 | Rouchouze |
| D705,799 S | 5/2014 | Funabashi et al. |
| D708,638 S | 7/2014 | Manzari et al. |
| D709,910 S | 7/2014 | Pasquero et al. |
| D711,897 S | 8/2014 | Chaudhri |
| D712,420 S | 9/2014 | Song et al. |
| D712,913 S | 9/2014 | Na |
| D717,825 S | 11/2014 | Pasquero et al. |
| 8,931,969 B2 | 1/2015 | Stewart et al. |
| D737,328 S | 8/2015 | Watson et al. |
| D738,903 S | 9/2015 | Lee |
| D739,861 S | 9/2015 | Perez et al. |
| D742,872 S | 11/2015 | Akana et al. |
| 9,195,818 B2 | 11/2015 | Ferren |
| D746,833 S | 1/2016 | Kim et al. |
| 9,235,271 B2 | 1/2016 | Berg |
| D749,085 S | 2/2016 | Furue et al. |
| D750,649 S | 3/2016 | Jung et al. |
| D754,719 S | 4/2016 | Zha |
| D755,809 S | 5/2016 | Kim et al. |
| D757,098 S | 5/2016 | Ekholm et al. |
| D758,411 S | 6/2016 | Lee |
| D758,417 S | 6/2016 | Chaudhri et al. |
| D758,427 S | 6/2016 | Park et al. |
| D759,095 S | 6/2016 | Seo et al. |
| D759,096 S | 6/2016 | Seo et al. |
| D763,890 S | 8/2016 | Pan |
| D765,671 S | 9/2016 | Katopis |
| D765,708 S | 9/2016 | Gagnier |
| D765,721 S | 9/2016 | Senders |
| D767,609 S | 9/2016 | Mehrzad |
| D769,934 S | 10/2016 | Chaudhri et al. |
| D771,089 S | 11/2016 | Guntzer et al. |
| D774,525 S | 12/2016 | Seo et al. |
| D775,171 S | 12/2016 | Gottlieb |
| D775,649 S | 1/2017 | Anzures et al. |
| D775,655 S | 1/2017 | Ibsies |
| D776,133 S | 1/2017 | Hill et al. |
| D777,202 S | 1/2017 | Maeda et al. |
| D778,927 S | 2/2017 | Bertnick et al. |
| D779,536 S | 2/2017 | Wingate-Whyte et al. |
| D779,558 S | 2/2017 | Ibsies |
| D780,198 S | 2/2017 | Cao |
| D780,200 S | 2/2017 | Chaudhri |
| D780,800 S | 3/2017 | Bi |
| D781,339 S | 3/2017 | Li et al. |
| D781,872 S | 3/2017 | Wu et al. |
| D786,927 S | 5/2017 | Ibsies |
| D787,555 S | 5/2017 | Ibsies |
| D788,153 S | 5/2017 | Kim et al. |
| D789,378 S | 6/2017 | Gottlieb |
| D790,569 S | 6/2017 | Anzures et al. |
| D797,766 S | 9/2017 | Ibsies |
| D798,894 S | 10/2017 | Ibsies |
| 2002/0178032 A1 * | 11/2002 | Benn ..................... A61C 19/00 705/2 |
| 2004/0015327 A1 | 1/2004 | Sachdeva et al. |
| 2004/0036632 A1 | 2/2004 | Ford |
| 2004/0095507 A1 * | 5/2004 | Bishop ............... H04N 1/00283 348/441 |
| 2004/0158507 A1 | 8/2004 | Meek, Jr. et al. |
| 2004/0236608 A1 | 11/2004 | Ruggio et al. |
| 2005/0043970 A1 | 2/2005 | Hsieh |
| 2005/0286953 A1 | 12/2005 | Griffin |
| 2007/0128574 A1 | 6/2007 | Kuo et al. |
| 2007/0239488 A1 * | 10/2007 | DeRosso ............... G06F 19/321 705/3 |
| 2007/0244581 A1 | 10/2007 | Nyholm |
| 2008/0018598 A1 * | 1/2008 | Marsden ............ A61B 1/00039 345/158 |
| 2009/0027334 A1 | 1/2009 | Foulk et al. |
| 2009/0183098 A1 | 7/2009 | Casparian et al. |
| 2010/0121658 A1 * | 5/2010 | Kaminski ............... A61C 19/00 705/3 |
| 2011/0043451 A1 | 2/2011 | Ibsies |
| 2012/0032945 A1 | 2/2012 | Dare et al. |
| 2012/0120181 A1 | 5/2012 | Kanalakis, Jr. et al. |
| 2012/0194546 A1 | 8/2012 | Ibsies |
| 2012/0274661 A1 | 11/2012 | Ye et al. |
| 2014/0002364 A1 | 1/2014 | Ibsies |
| 2014/0337049 A1 | 11/2014 | DeBusk et al. |
| 2015/0135108 A1 | 5/2015 | Pope et al. |

FOREIGN PATENT DOCUMENTS

| | | |
|---|---|---|
| WO | WO02091279 | 11/2002 |
| WO | WO2002091279 | 11/2002 |

(56) References Cited

FOREIGN PATENT DOCUMENTS

WO    WO2014086691    6/2014

OTHER PUBLICATIONS

Datacon Dental Systems, "Charting Overview," at least as early as May 4, 2015, web site, http://www.datacondental.com/charting-overview, 1 page.

Dental Equipment Center, "Dental Equipment Store—Kavo Dental Equipment," at least as early as Jun. 29, 2015, web site, http://www.dentalequipmentcenter.com/kavo-dental.html, 3 pages.

Dentimax, "DentiMax Software," as early as May 4, 2015, web site, http://www.softwareadvice.corn, 1 page.

Health and Medicine, Spinoff 2008, "Periodontal Probe Improves Exams, Alleviates Pain," Originating Technology/NASA Contribution, at least as early as 2008,. 2 pages.

Perio-Imaging, "Periodontal Gum Disease," at least as early as Jun. 29, 2015, web site, http://www.perioimaging.com/pages/products.aspx, © 2008 Perio-Imaging Inc., all rights reserved, 11 pages.

Probeone, "The Gentle Probe," at least as early as Jun. 29, 2015, © 1995-2011 Probe One, web site, http://www.probeone.com/standardized.htm, 2 pages.

Technology Transfer Program, Bringing NASA Technology Down to Earth, "Periodontal Probe Improves Exams, Alleviates Pain," at least as early as Jun. 29, 2015, web site, https://spinoff.nasa.gov/Spinoff2008/hm_8.html, 2 pages.

Unident Software Company, "Axex Dental Software," web site, at least as early as May 4, 2015, http://www.softwareadvice.com, 1 page.

Krantz, Peter, "The Ideal VIM Keyboard," at least as early as Nov. 11, 2016, http://www.peterkranz.com/2006/vim-keyboard/, 7 pages.

DenChart Periodontal Software, "DenChart comes packed with features and power tools," http://www.denchart.com/features, Internet Archive WayBackMachine, at least as early as Dec. 15, 2009, 2 pages.

United States Patent and Trademark Office, "U.S. Appl. No. 61/113,822," Provisional of 2010/0121658, Kaminski, et al., filed Nov. 12, 2008, 29 pages.

* cited by examiner

FIG. 9
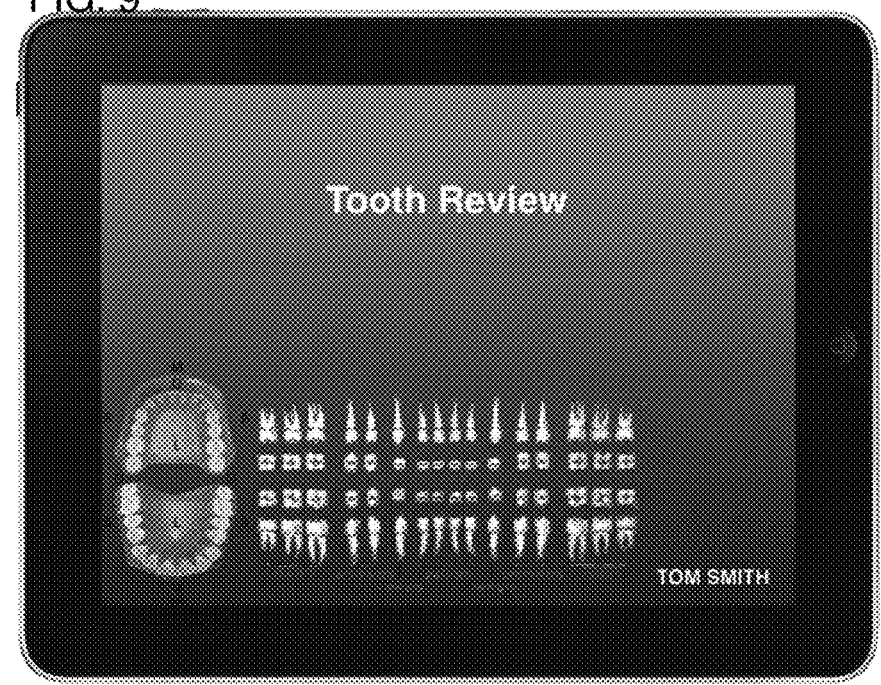
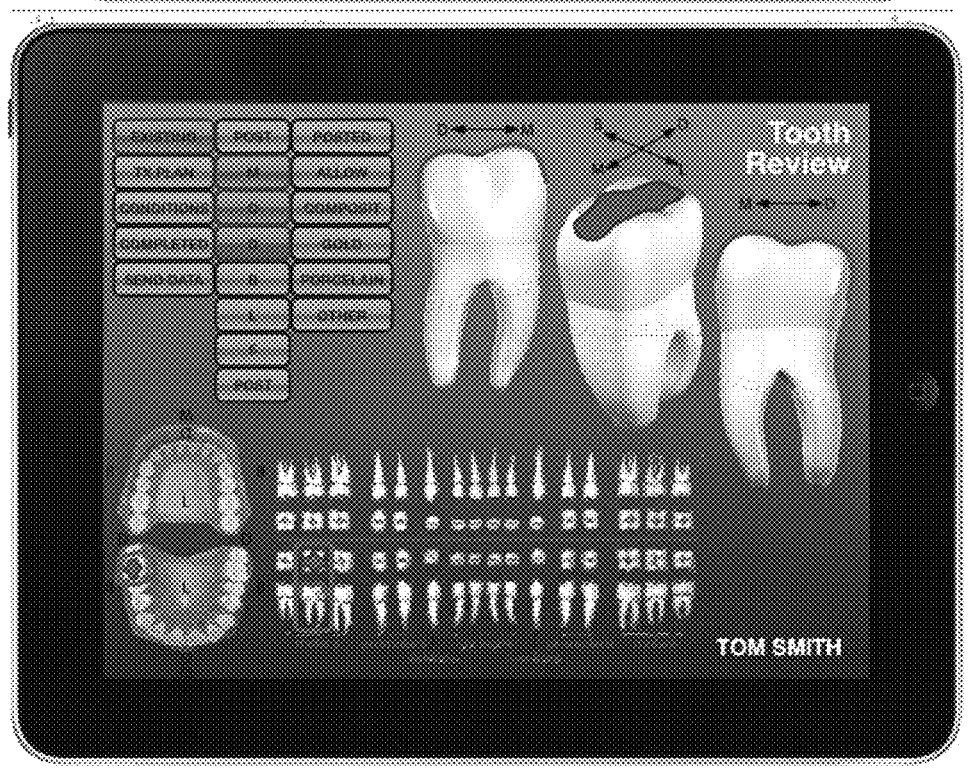
FIG. 10

SPECIALIZED KEYBOARD FOR DENTAL EXAMINATIONS

PRIORITY CLAIM

This application is a continuation in part of earlier filed, non-provisional and co-pending U.S. patent application Ser. No. 12/544,074, which was filed on Aug. 19, 2009 by the same inventor. The present application is based on and claims priority from this application pursuant to 35 U.S.C. § 120 and that disclosure is hereby expressly incorporated herein by reference.

BACKGROUND OF THE INVENTION

This invention relates to specialized input devices, specifically a keyboard and method of use, and software related to periodontal examinations.

A periodontal examination, an important procedure performed frequently in dental and periodontal offices, includes an examination of the bones holding the teeth in place and the conditions of the teeth and gums. The examination includes probing the teeth and the gums around each of the patient's teeth in succession, and recording the results. Because the examination requires several measurements for each of the (normally) 32 teeth, a large amount of data is generated and must be recorded.

The data output from the examination of a patient is recorded on a chart. Today, the dental chart—no longer a paper record hand-written by the dentist—is a computerized system including a user interface, input device, and database. Accordingly, today's dentist electronically inputs a patient's dental examination into a computerized record associated with the patient. This record requires the dentist or assistant to input the patient exam. Preferably, this input occurs in real-time to avoid errors and reduce inefficient duplication of effort.

However, real-time data entry, while also maintaining a safe and clean environment free of risk of contamination of infectious disease, requires a time intensive operation requiring two persons (examiner and data-entry person). In some instances, specialized tools are used to facilitate the exam and real-time data recording, but most often a standard keyboard and/or touch-screen and/or mouse, or other point-and-click input device is used by the assistant while the dentist probes and examines each tooth and audibly notes the condition. In turn, the assistant keys in the audible notes via a standard keyboard or touch-screen into the electronic chart for the dental patient.

This dental chart often includes notations and records of the locations of carious, broken, and missing teeth. The dental chart also includes notations and records of work previously performed by another dentist, including restorations, crowns, and bridges. To improve efficiencies, various prior art methods and devices have been introduced to record and retain patient records on a varied form of the dental chart.

One such improvement is described in U.S. Pat. No. 7,343,305 granted to Benn et al. on Mar. 11, 2008. Benn et al. teach a method and system for charting tooth decay and disclose a conventional input device and computer for entering tooth conditions during an examination. Particularly, this reference discloses a method and system for advanced caries management that provides more descriptive representations of tooth decay, including site severity, activity (demineralization or remineralization), and cavitation state (non-cavitated or cavitated) of decay. Benn et al. teach a need in the art for a simple graphical user interface (GUI) to make entering and viewing data relative to caries management easier. A conventional GUI display includes a desktop metaphor upon which one or more icons, application windows, or other graphical objects are displayed. Typically, a user interacts with a GUI display utilizing a graphical pointer, which the user controls with a graphical pointing device, such as a mouse, touch pen, trackball, or joystick. The user selects icons or other graphical objects within the GUI display by positioning the graphical pointer over the graphical object and depressing a button associated with the graphical pointing device. In addition, the user can typically relocate icons, application windows, and other graphical objects on the desktop utilizing the well-known drag-and-drop techniques. By manipulating the graphical objects within the GUI display, the user can control the underlying hardware devices and software objects represented by the graphical objects in a graphical and intuitive manner.

Other known methods and devices relating particularly to input devices are described in U.S. Pat. No. 5,752,827 issued on May 19, 1998 to Baron et al. Baron et al. teach a specialized input keyboard specifically adapted for inputting tooth conditions during a dental examination. FIGS. 3, 4, 5, 6, and 7 of the Baron et al. reference show a generally rectilinear, thin, portable, input keyboard with standard alpha-numeric keys arranged in a conventional row/column layout. Baron et al. further teach a method of special codes representing combinations of a tooth and a condition.

U.S. Pat. No. 7,354,402 issued on Apr. 8, 2008 to Hoarau et al. teaches an intra-oral data input tool including a discoid head and handle. The discoid head includes a data input device responsive to force applied by a stylus and may be used directly by contacting a tooth during a dental examination.

Yet other methods and devices, relating particularly to output or display improvement, include U.S. Pat. No. 5,944,531 issued on Aug. 31, 1999 to Foley et al., which teaches an instructional display of a human mouth; and U.S. Pat. No. 6,664,986 issued on Dec. 16, 2003 to Kopelman et al., which teaches a graphical user interface and display of a representation of a human mouth in simulated 3-D.

One improved input device for periodontal examinations includes the teaching of Baron et al. in U.S. Pat. No. 5,752,827 issued on May 19, 1998. Baron et al. teach an automated periodontal examination data recording and recall apparatus having at least one pre-programmed mode of operation. Periodontal examination data is entered in a predetermined sequence into the Baron et al. apparatus. The periodontal examination must be performed in a predetermined sequence. The periodontal examination apparatus includes a keypad input device, an LCD, a main controller, and an attachment device for securing the apparatus to the examiner's arm.

Despite the attempts at improving the methods and devices to improve efficiency of data collection during a dental examination, there remains a need for an easy-to-use, customized or specialized keyboard that enables rapid data entry in any sequence tailored to the needs of a periodontal examination. Such a keyboard must adapt to existing computer hardware and software systems commonly used in dental offices.

SUMMARY OF THE INVENTION

The present invention, in various preferred embodiments, includes an input device for use with a computerized system.

Additionally, a method of use of a keyboard can be implemented in numerous ways including as a component of a computer or database system, a method of data input, an apparatus, an apparatus connected to a computer readable medium, a computer program product, or a data structure tangibly fixed in a computer readable memory. Several embodiments of the invention are discussed below.

As a computer system, an embodiment of the invention includes a memory unit containing data, a display, and a processor unit. The system may be, for example, in the form of a desktop, laptop, handheld, or palm-sized device, a personal data assistant (PDA), or integrated with other devices. The display has at least one display area (window). The processor unit operates to receive input from the user (via, e.g., a keyboard, mouse, pen, voice, touch-screen, or any other means by which a human can input data into a computer, including through other programs such as application programs or devices such as a probe), store the input as data, and output the data to the screen or printer. The data may also be transmitted to another device, such as a computer, or transferred via electronic means (including Internet communications). The memory unit may store the protocol for the method of recording carious lesions. The display device may include icons representative of the method of the present invention. The computer system further includes a graphical user interface (GUI) for the display screen for searching, inputting, and displaying data. A variety of formats for searching, inputting, and displaying data are contemplated.

In one preferred embodiment, a graphical representation of all of the teeth of a patient is displayed on a device (such as a computer screen) from which a specific tooth is selected via the specialized keyboard of the present invention. That tooth is then displayed with individual anatomical graphical regions delineated. The region on the display that corresponds to the region on the actual tooth being examined is selected (or the regions can be automatically activated in a predetermined order). If using a digital probe, the reading on the probe is recorded (directly or manually) for the selected region on the screen. If manual probing is conducted, the operator enters the appropriate data for that region. Voice recognition and voice output may be used in conjunction with the method. Readings are recorded for each region as necessary. The process is repeated for each tooth as necessary. A printout of the chart can be provided from the device or from a central system with which the device communicates (e.g., PDA synchronized with desktop).

As a computer readable media containing program instructions, an embodiment of the invention includes computer readable code devices for the specific operations of the invention, including graphical display of the teeth, unique display of regions for systematic examination, input of data (manually or directly from another instrument), recording of data, display of data, and output of data. The methods of the present invention may be implemented as a computer program product with a computer-readable medium having code thereon. The program product includes a program and a signal bearing media bearing the program.

As an apparatus, the present invention may include at least one specialized keyboard coupled to a processor, a memory coupled to the processor, and a program residing in the memory which implements the methods of the present invention.

One preferred embodiment of the present invention includes an apparatus including a specialized dental keyboard. This keyboard will revolutionize the way data is entered in all dental offices and schools by reducing error due to misdiagnosis and increase the accuracy of data entry of patient's existing conditions prior to rendering treatment. This data entry device seamlessly integrates with existing patient management software via key macros and direct software bridging. The keyboard includes keys (separate keys or combinations of keys) representing all teeth numbers, including primary teeth, based on the Universal/National System primarily used in the United States.

The Universal/National System for permanent (adult) dentition (1-32) starts at the patient's upper right molar (1) and follows around the upper arch to the upper left third molar (16), descending to the lower left third molar (17) and follows around the lower arch to the lower right third molar (32). The Universal/National System order for the primary (baby) dentition is the same as described for the permanent dentition, however, the primary teeth are designated by upper case letters A through T, with A being the patient's upper right second primary molar and T being the lower right second primary molar.

Accordingly, the present invention utilizes this Universal/National System and functions as an improved dental pathosis and treatment plan entry device. The present invention enables the operator (such as a dental assistant, dental hygienist, or a dentist, for example) to enter data into pre-determined software, linked via a software bridge. And, key-macros make the entry of data more accurate, providing protection for both the dentist and the patient as far as the data entry is concerned. This data provides the existing conditions present in the patient's mouth and the treatment plan needed to correct these conditions. The patient will be able to have a complete diagnosis and have a better understanding of the conditions that exist in his mouth. This device enables connection to certain educational videos that the patient will be able to benefit from and get a better understanding of the need for the recommended treatment. This device improves the data-entry operation for a tooth and includes short cuts (keys and/or macros) for existing conditions, a link with intraoral images of the tooth, a link with the periodontal assessment of the tooth, and is able to select any combination of several different treatment options including placement of the correct fees for each procedure and American Dental Association (ADA) codes for each procedure.

The keyboard of the present invention, therefore, better enables a doctor or dentist to efficiently create a record of past work ("what was done" or "existing"), what needs to be done, why it needs to be done, and the long term prognosis of the procedure based on the periodontal health of the tooth—all the essential data a board of dentistry requires to protect both the patient and the doctor. This device can become the educational tool of the future if schools were to carry this device and make incoming dental students use it as the standard of care in data entry.

This keyboard works with existing dental software tools that are available on the market and it will be made compatible via software bridges or patches, or in the future—software can be specifically developed for it. One example of existing software for which the present invention is well suited includes the DENTRIX®-brand software tool available from http://www.dentrix.com, which is a readily available dental software tool and is well known in this art. Other examples of compatible software include the EAGLESOFT®-brand (available from http://patterson.eaglesoft.net/index.htm), DAISY DENTAL™ Software (available from http://www.daisydental.com/software/index.shtml), and KODAK®-brand dental software (available from http://www.kodakdental.com/for-dentists/practice-management-systems/softdent.aspx).

The present invention includes a keyboard with specific buttons (tooth identifying keys). Each button represents a tooth on the two rows of keys including a shift-like key on the right side that toggles between primary and permanent teeth. On the left side is the dental diagnosis and treatment section. The following symbols and abbreviations are used: EX=existing condition, whether it is a filling (type of filling), broken half of tooth, or decay on a certain spot on the tooth; DX=what is wrong with the tooth, and why it needs treatment, for example a failing alloy filling, open margins, or recurrent decay on mesial; and TX=recommended treatment; for example, the proposed treatment, such as a crown, gold inlay, porcelain inlay, or composite filling. There will be a toggle to choose different options of treatment, such as a root canal on tooth #30 or a removal of tooth #30, and treatment plan—for example, an implant.

When a user presses the probing chart key, the computer will automatically pull up the patient's periodontal chart. On the right side of the device is the periodontal health of the tooth. It is represented with the most common buttons for millimeter readings of the periodontal pockets, for example from 1 mm to 6 mm and the less common measurements are represented with smaller buttons, for example from 7 mm to 12 mm for each tooth. A bleeding point button can be pressed for the mesial, middle reading, and distal reading. As an example, tooth #2 has a facial reading of 3-5-4, bleeding points on both mesial and middle readings, and class I mobility. The sequence of buttons that will be pressed include the #2 button on the upper left (to select tooth #2), followed the bleeding point button, the numbers 3-5-4 of the probing buttons, the mobility button, and the class I button. This will give a very accurate reading of the existing periodontal condition of tooth #2.

Pressing the image capture button causes the computer to pull up the intra-oral camera.

One contemplated method includes using the keyboard to assist with dental photographs (pictures). Accordingly, the way pictures will be taken is the assistant, for example, will press the #4 key and the camera will be activated to point to tooth #4 and the image will be stored in the patient's computer chart as tooth #4. Thus, when data is pulled for tooth #4, there will be an existing condition of what the patient's tooth looked like when he first joined the practice, along with an image of the tooth, the periodontal health of the tooth, what the proposed treatment was at the time, and the treatment that was rendered on the tooth.

An assistant, doctor, or hygienist can enter a full treatment plan on this keyboard without having to use a mouse. Using a mouse in the dental operatory is awkward, at best, and tends to really slow down the data entry, which causes the assistant to skip over pertinent data.

The LCD display displays the data entered and has a 2 second time lapse so that data can be reviewed prior to having it sent to the software. This way the person entering the data can intercept it and change it if he/she sees that they made a mistake in the data entry.

One embodiment of the present invention contemplates a specialized dental keyboard/input-output device adapted for use with a host computer to record conditions of teeth in a patient during a dental exam using a dental examination software tool resident on the host computer. The device includes a wired or wireless connection coupled to the host computer for sending inputted data representing a plurality of keystrokes; a set of programming sequences resident on the host computer adapted to convert the inputted keystrokes to a data string recognizable by the dental examination software tool; a plurality of input keys arranged on a keyboard, each key communicating to the wired or wireless connection; and a liquid-crystal display screen mounted on the keyboard and adapted to display a sequence of keystrokes.

This embodiment further contemplates that the plurality of input keys consists of at least 32 keys wherein each key is consecutively numbered beginning with digit "1" and ending with the combination digits "32" indicating each one of the thirty-two teeth.

This embodiment further contemplates a first-condition key on the keyboard and a second condition key wherein the first condition key represents the patient's current condition and a second condition key represents the patient's prescribed treatment.

This embodiment further contemplates a second multidirectional input element having at least five unique input directions. The five input directions are disposed generally in a common input plane. And, the plurality of input keys includes a first set of keys numbered from 1 to 32, the first set of keys being adapted to input the current condition of the patient's teeth; and a second set of keys numbered from 1 to 32, the second set of keys being adapted to input the treatment or prescribed treatment of the patient's teeth.

This embodiment further contemplates that the keys also include an RCT (Root Canal Therapy) key; a PFM (Porcelain Fused to Metal crown) key; an FGC (Full Gold Crown) key; an A.Prophy (Adult Prophy) key; a C.Prophy (Child Prophy) key; an SRP (Scaling and Root Planing) key; a Pontic (middle fake tooth on a bridge) key; a Part Denture (partial denture) key and a Full Denture (complete denture, no teeth on upper or lower arch).

This embodiment further contemplates that the keys also include an F (Facial or Buccal) key; an L (Lingual or Palatal, that is palate side or tongue side) key; a D (Distal, the back side of the tooth) key; an M (Mesial, the front side of the tooth) key; and an I/O (Incisal or Occlusal, the top side of the tooth or the chewing surface of the tooth—in the anterior teeth case that is called incisal) key.

This embodiment further contemplates a method for examining a patient's teeth during a dental exam. The method includes providing a specialized dental keyboard having a plurality of keys, the plurality of keys including at least 32 keys wherein each key is consecutively numbered beginning with digit "1" and ending with the combination digits "32" indicating each one of the thirty-two teeth and at least one additional key from the following group: an RCT (Root Canal Therapy) key, a PFM (Porcelain Fused to Metal crown) key, an FGC (Full Gold Crown) key, an A.Prophy (Adult Prophy) key, a C.Prophy (Child Prophy) key, an SRP (Scaling and Root Planning) key, a Pontic (middle fake tooth on a bridge) key, a Part Denture (partial denture) key, or a Full Denture (complete denture, no teeth on upper or lower arch key); providing a host computer with a dental examination software tool resident in memory; providing a software macro installed on the host computer, the software macro adapted to translate keystrokes of the specialized dental keyboard to data strings for inputting into the dental examination software tool; and inputting a sequence of keystrokes on the dental keyboard, the sequence of keystrokes representing a condition observed during the dental exam.

BRIEF DESCRIPTION OF THE SEVERAL VIEWS OF THE DRAWINGS

FIG. 9 is another screen shot of a virtual keyboard and graphical user interface on the touch-screen tablet as contemplated by the second embodiment of the present invention.

FIG. 10 is another screen shot of a virtual keyboard and graphical user interface on the touch-screen tablet as contemplated by the second embodiment of the present invention.

DETAILED DESCRIPTION OF THE INVENTION

Possible embodiments will now be described with reference to the drawings and those skilled in the art will understand that alternative configurations and combinations of components may be substituted without subtracting from the invention. Also, in some figures certain components are omitted to more clearly illustrate the invention.

Figure 1:
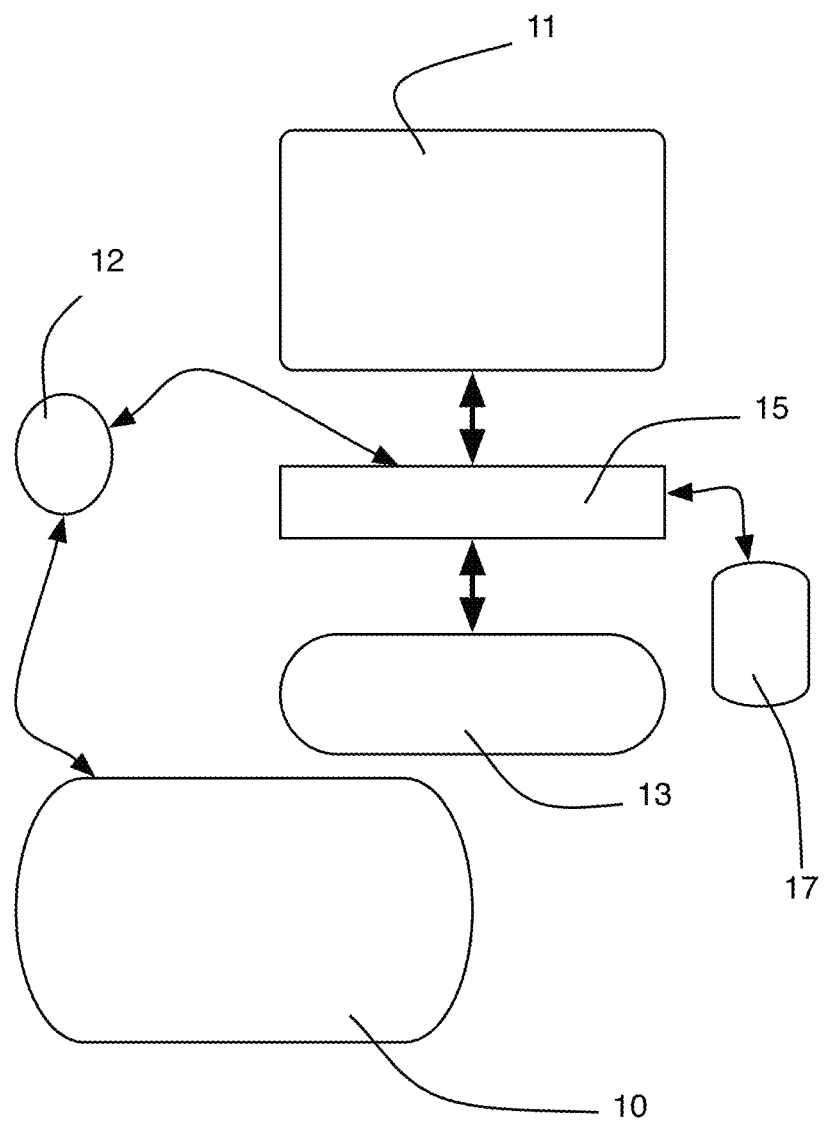
FIG. 1 is a system overview of one embodiment of the present invention.
Figure 3:
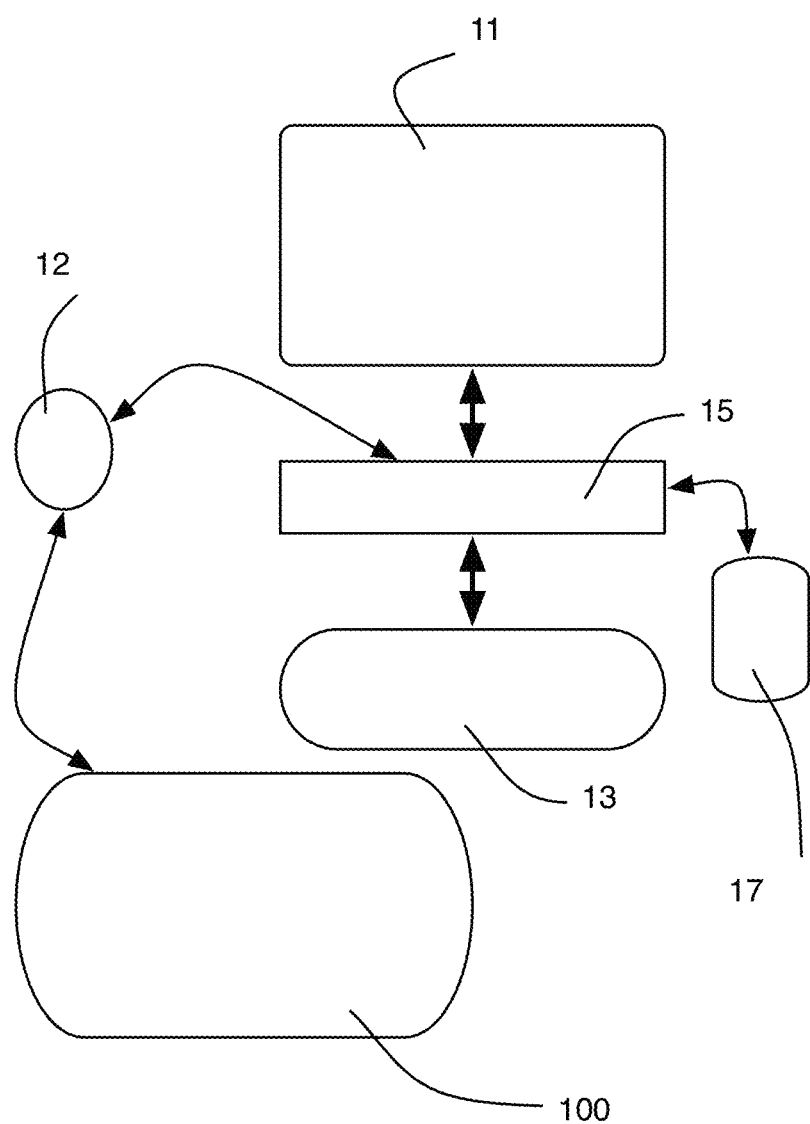
FIG. 3 is a system overview of a second embodiment of the present invention.
Figure 4:
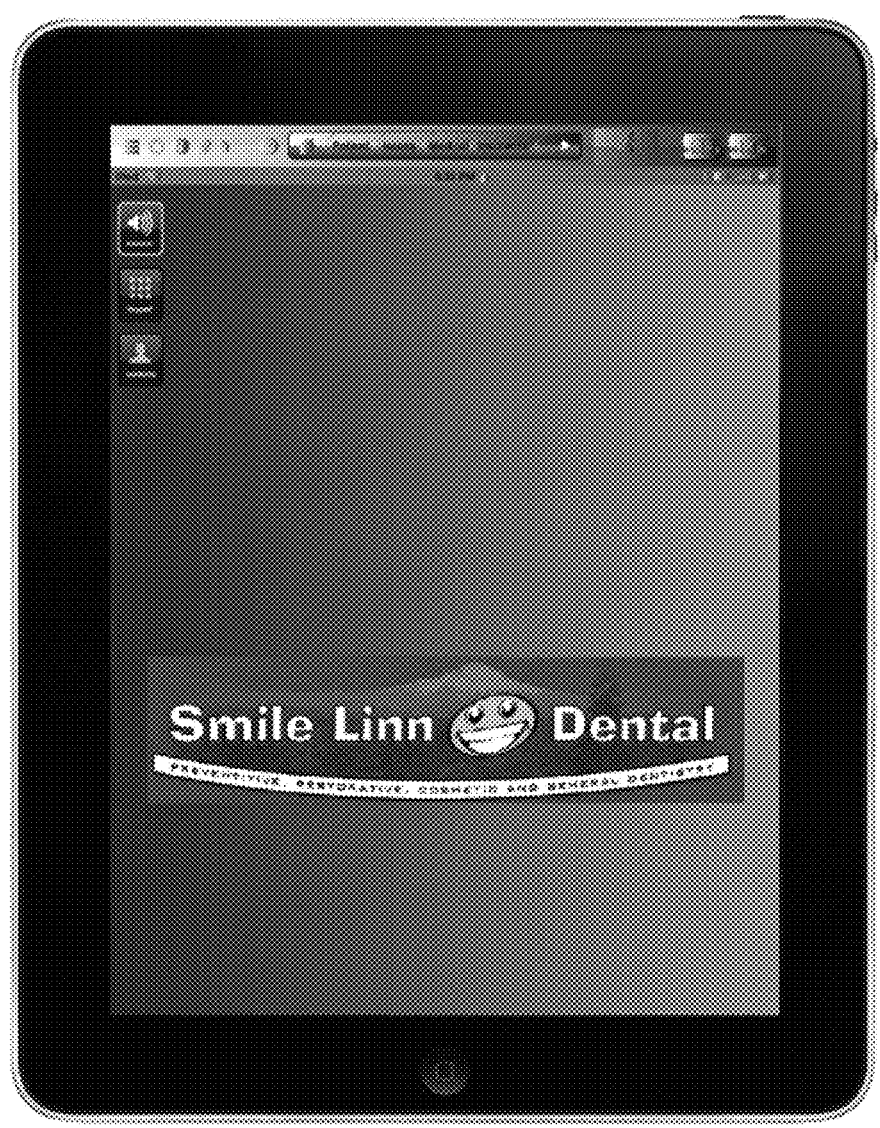
FIG. 4 is a virtual keyboard and graphical user interface combination of the present invention and shows an opening screen.
Figure 5:
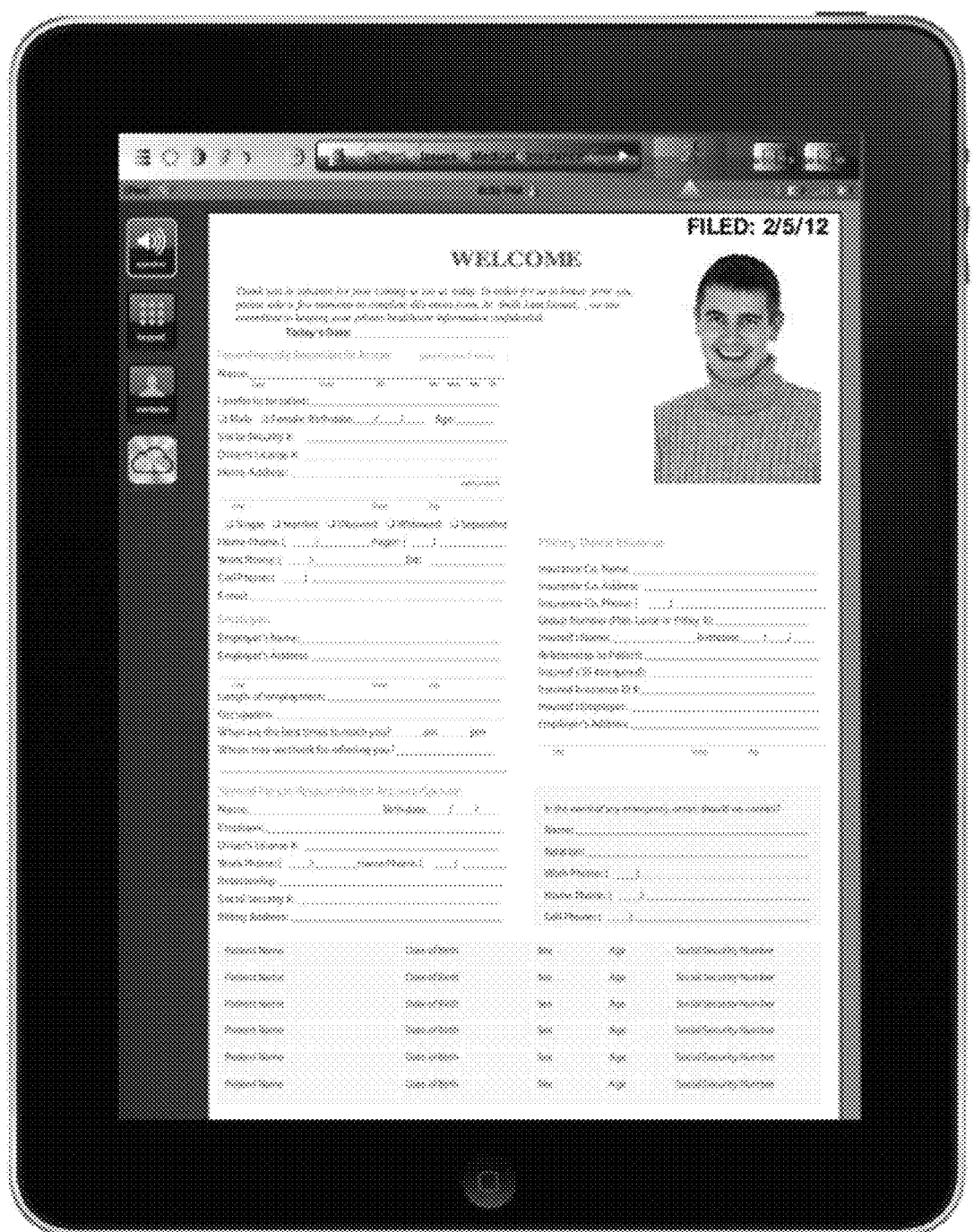
FIG. 5 is screen shot of a patient record on the touch-screen tablet as contemplated by the second embodiment of the present invention.
Figure 6:
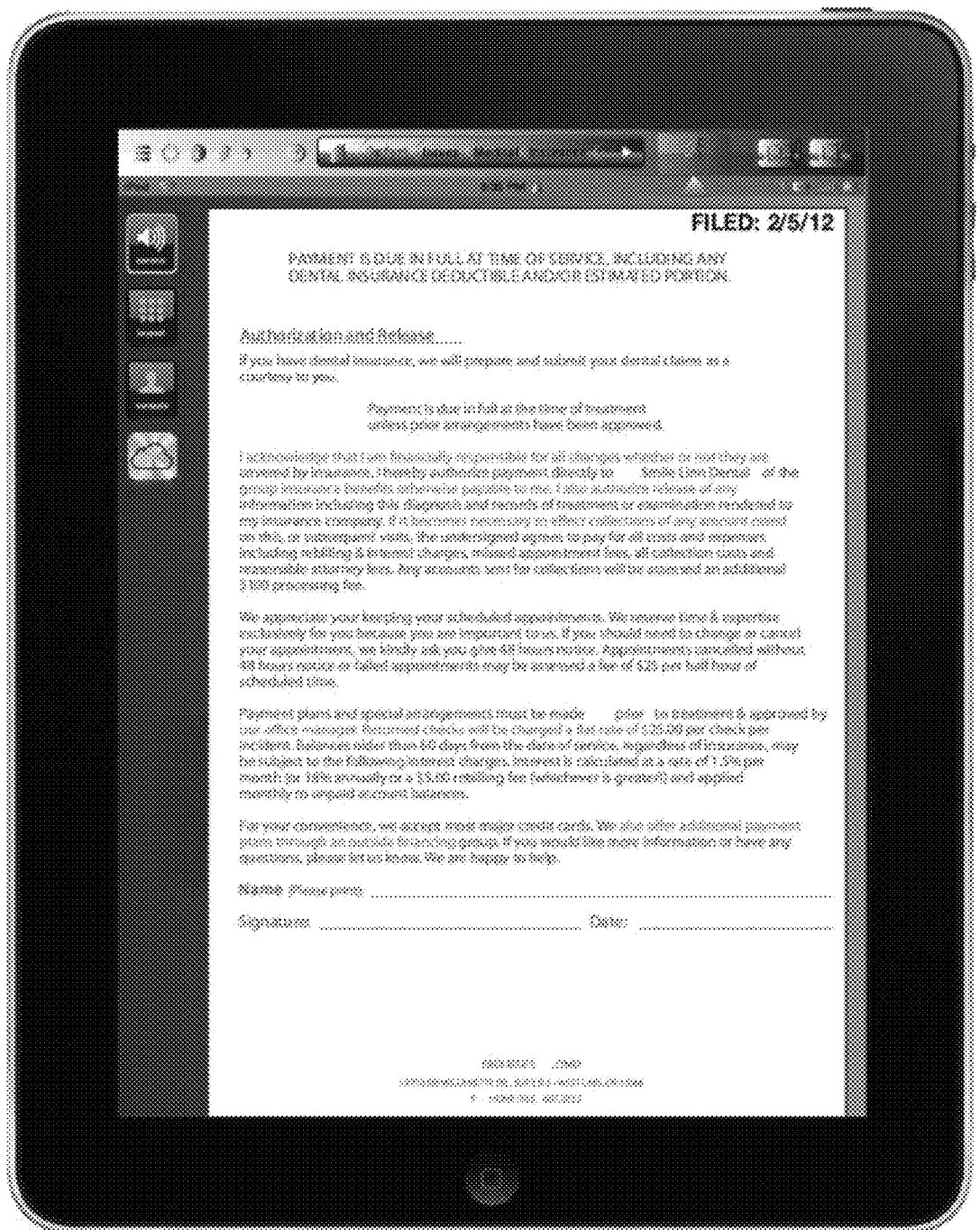
FIG. 6 is a screen shot of a patient disclosure form on the touch-screen tablet as contemplated by the second embodiment of the present invention.
Figure 7:
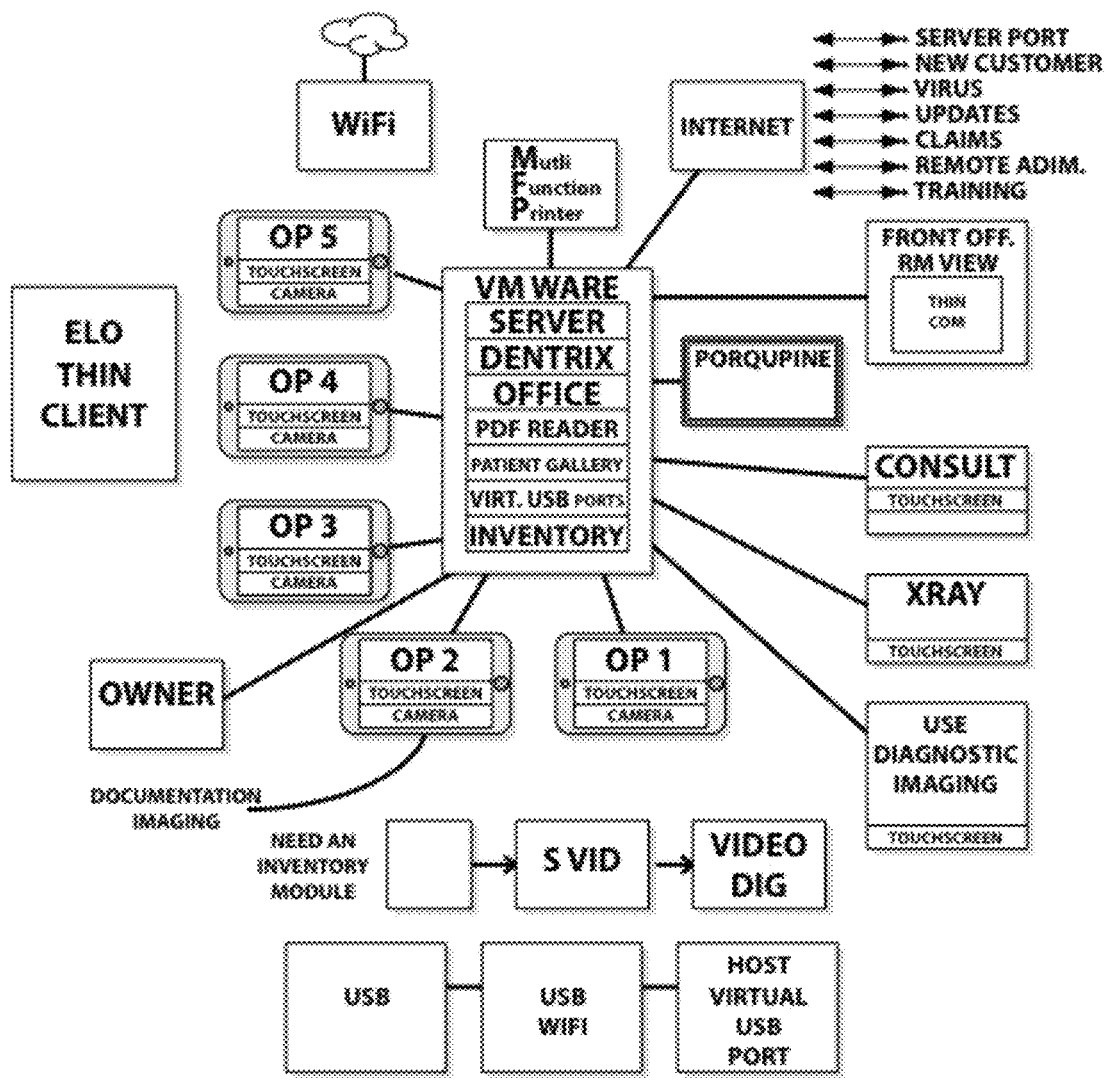
FIG. 7 is logic diagram of the virtual keyboard and software program of the second embodiment of the present invention.
Figure 8:
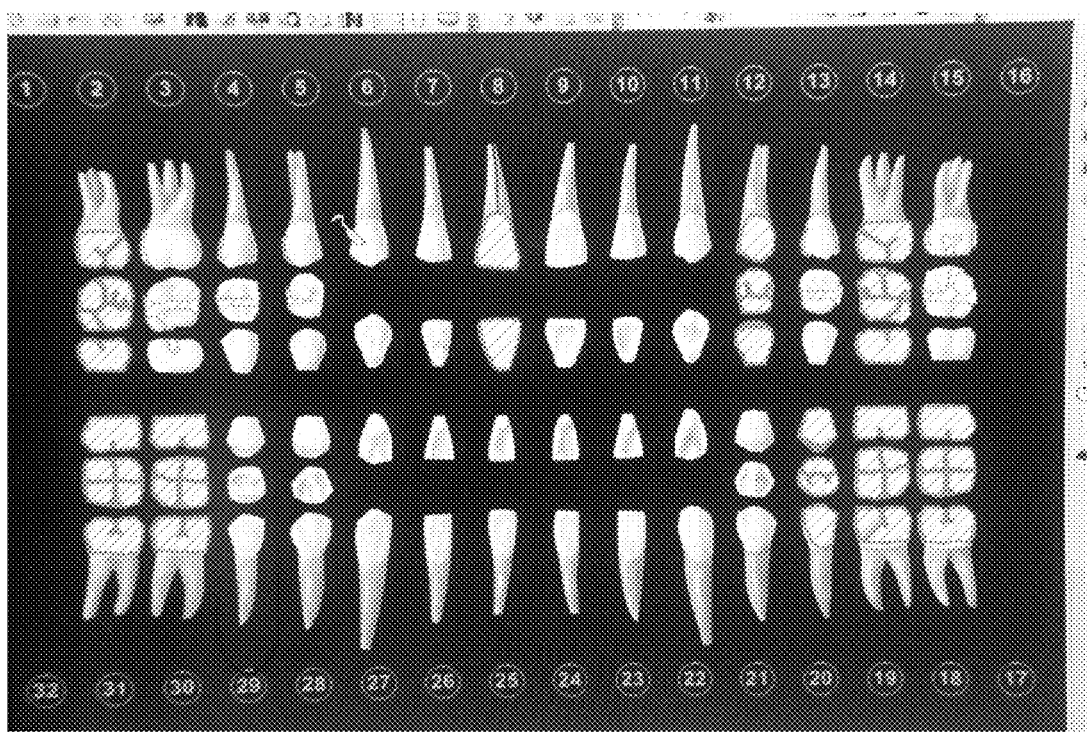
FIG. 8 is a possible virtual keyboard layout according to one embodiment of the present invention.
Figure 11:
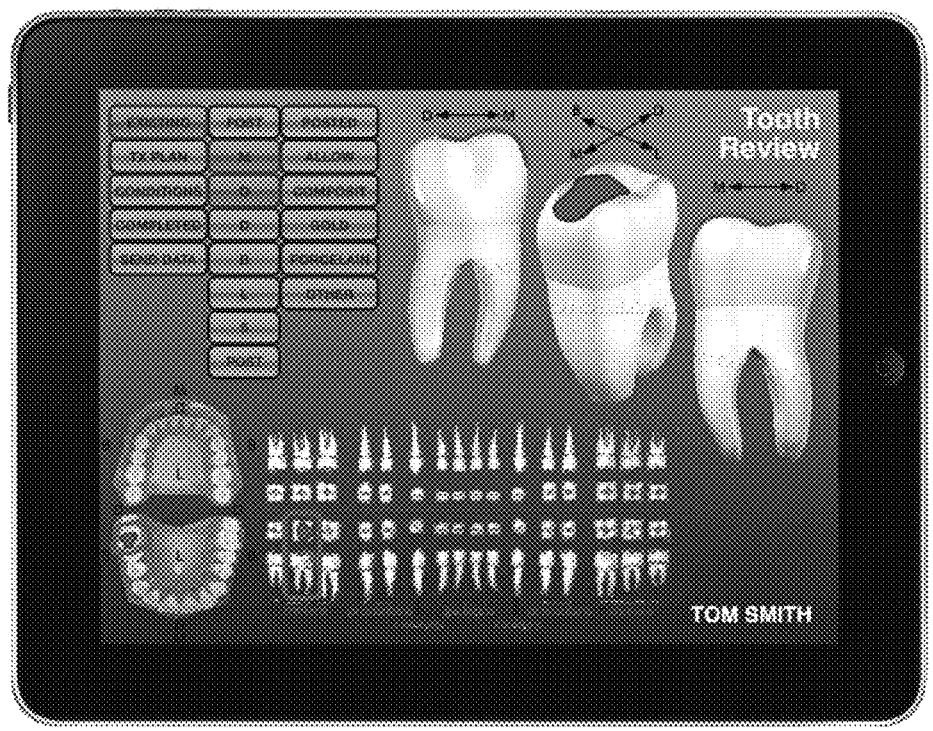
FIG. 11 is another screen shot of a virtual keyboard and graphical user interface on the touch-screen tablet as contemplated by the second embodiment of the present invention.
Figure 12:
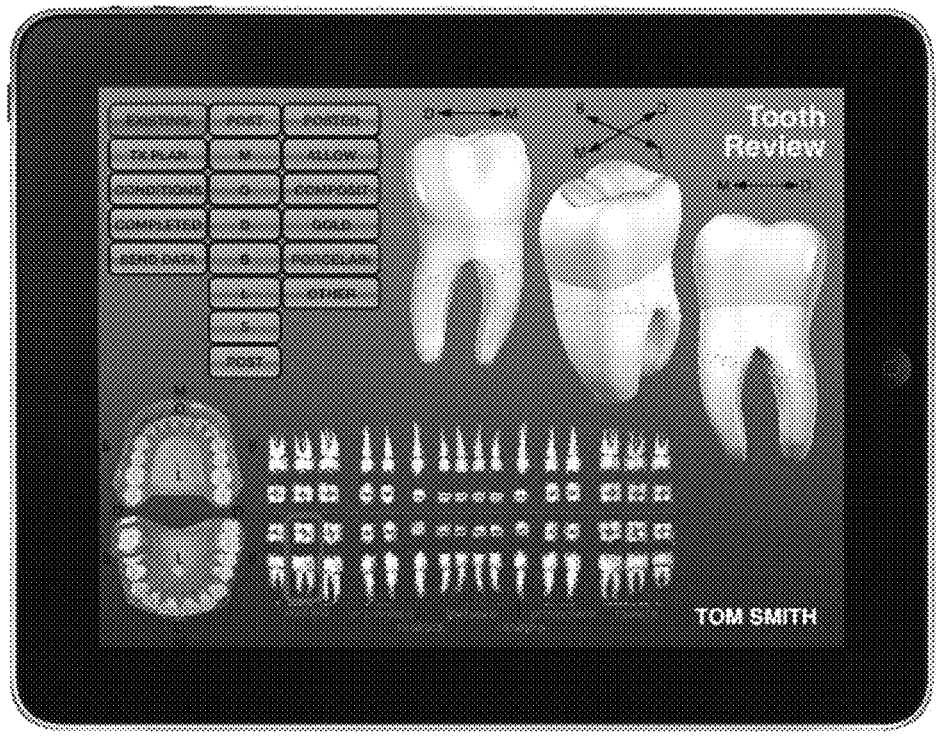
FIG. 12 is another screen shot of a virtual keyboard and graphical user interface on the touch-screen tablet as contemplated by the second embodiment of the present invention.

FIG. 1 illustrates a system utilizing a keyboard 10 according to a first preferred embodiment of the present invention. The specialized keyboard 10 or virtual keyboard 100 (see, for example, FIG. 3) on a touch-screen communicates bi-directionally with a central processor on a computer 15. The communication between the specialized keyboard 10 or virtual keyboard 100 on a touch-screen and computer 15 may be facilitated by a communication means 12, such as a wireless sending/receiving unit integrated (physically coupled to or physically integrated with) the specialized keyboard, such as a BLUETOOTH® enabled wireless transmitter/receiver. The traditional computer 15 includes a normal output device 11, such as a flat-panel display screen, CRT monitor, printer, and the like. And further, the computer 15 includes traditional input devices such as a keyboard 13 and mouse 17. An example of a suitable conventional computer system includes a desktop PC having an Intel Pentium-brand IV 2.4 GHz processing chip with 512 MB RAM-1 GB RAM, at least 2 GB available disk space a CD-ROM Drive, an Ethernet 10/100/1000 network card, a standard CRT/LCD monitor with a minimum of 1024×768 screen resolution, 3D capable DirectX 9 compatible graphics card with 128 MB video memory (needed for 3D Modeling), a USB Chipset with two or more powered USB 2.0 ports, additional PCI Express, AGP, PCI or USB 2.0 expansion slots may be required, and a WINDOWS®-brand XP Professional operating system, for example.

FIG. 1 shows the specialized keyboard 10 (or virtual keyboard 100 shown in FIG. 3) on a touch-screen as a separate physical entity from the communication means 12. It should be understood that the communication means includes, in one embodiment, a separate, "black box" device that has wired connection to the computer 15 and keyboard 10 and includes software and hardware to convert signals from the keyboard 10 to standard code sequences for the computer and resident software to use conventionally as if keyed from the traditional associated keyboard 13.

In use, the present invention keyboard will be used instead of conventional input devices (for example, a conventional keyboard, touch-screen, mouse, pointer or a combination of these). Built-in software macros pre-loaded on the host computer will interpret keystrokes from the keyboard of the present invention. The macros will then automatically feed the string of commands required by the specific software platform the dentist uses to manage patient care.

It should also be understood that the communication means 12, in an alternative embodiment, includes a wired or wireless link between the specialized keyboard 10 or virtual keyboard 100 on a touch-screen and the processor on a conventional computer 15.

Other examples of conventional computer systems include DELL® standard dental PC computers running either WINDOWS XP® or VISTA®. These systems commonly run dental software, such as DENTRIX®, EAGLE-SOFT®, DAISY DENTAL™, and KODAK® dental software including support for specialty dental software such as DOLPHIN IMAGING® dental software.

Figure 2:
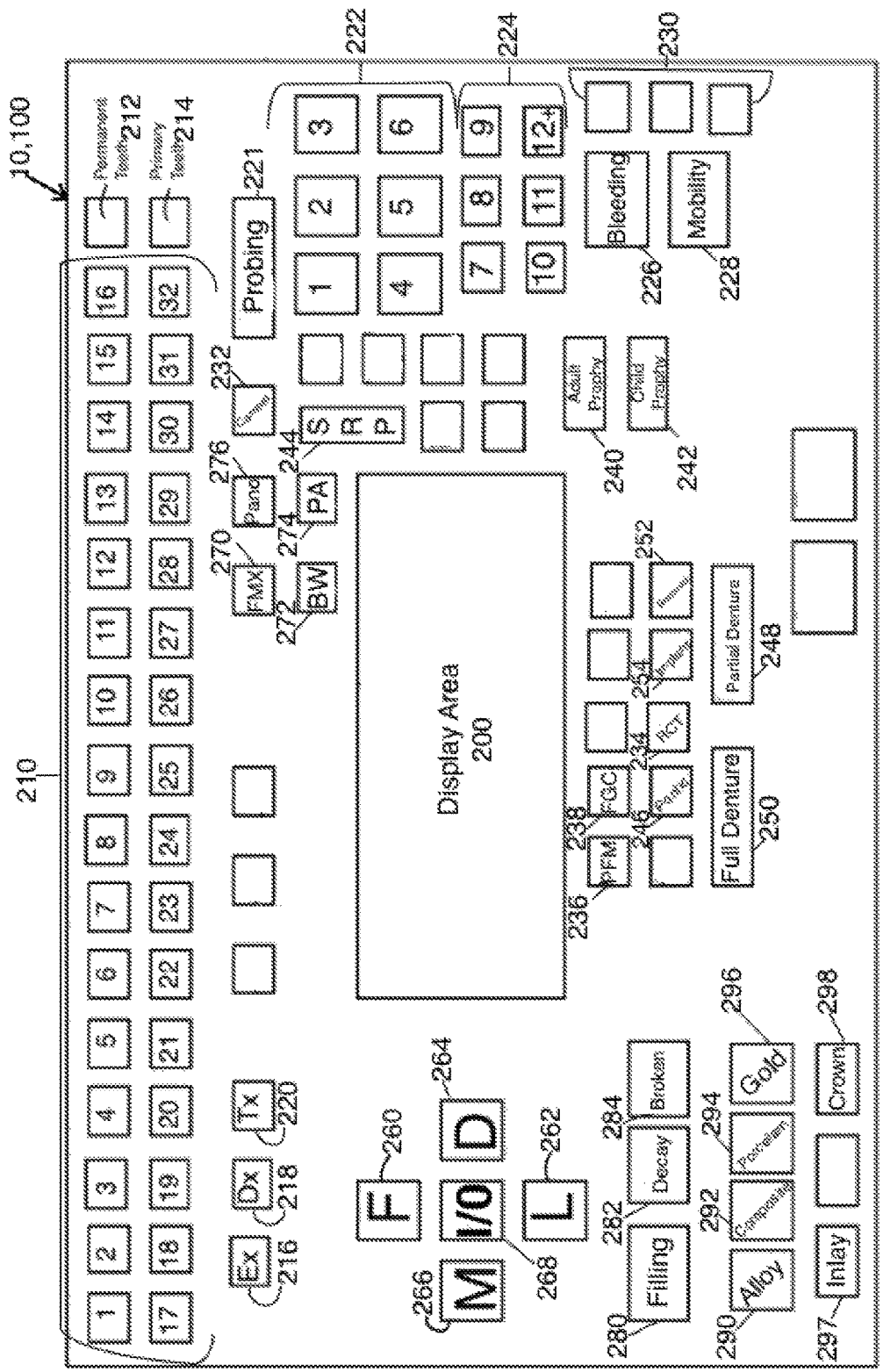
FIG. 2 is one possible keyboard layout or virtual key layout according to one embodiment of the present invention.

One contemplated layout for a specialized dental keyboard 10 according to the present invention, as FIG. 2 illustrates, includes an integrated display panel 200 (also referred to herein as a display area or window) and a plurality of specialized keys. One suitable display panel includes a device made by Samsung Electronics Co., Ltd. of Seoul, Korea and includes a design optimized for mobile applications consisting of a 7 inch diagonal viewing screen with a Si-TFT LCD Model that uses transparent plastic substrate that maintains constant thickness and will not break, even when bent. A full-color display delivers 640× 480×RBG (114 ppi) resolution with aperture ratio of 40%, brightness rating of 100 nit, and color saturation of 60% of NTSC, for example. The display panel 200 is used to flash the buttons pressed on the LCD screen for a couple of seconds to verify the data being sent to the computer, giving the operator a chance to verify that the correct data is sent to the computer or to cancel and reenter the data by pressing a cancel button.

The specialized keyboard 10 or virtual keyboard 100 on a touch-screen includes a plurality of tooth identifying keys (reference number 210). This plurality of tooth identifying keys 210 consist of a first row of 17 keys and a second row of 17 keys, the first row being consecutively numbered from 1 to 16 representing the correspondingly numbered teeth in a human mouth, plus one additional key to denote permanent teeth (reference number 212). The second row is reverse consecutively numbered from 32 to 17 representing the remaining teeth, plus one additional key to denote primary (baby) teeth (reference number 214). The sequence of keys in the plurality of tooth identifying keys 210 is visually arranged as commonly displayed in graphical representations of teeth, which is quite familiar to dentists.

Additional individual keys are provided on the keyboard 10 including an "EX" key 216 for indicating the current condition of the tooth, a "DX" key 218 for indicating the diagnosis of the tooth, and a "TX" key 220 for indicating the prescribed treatment of the tooth. As set forth in the Summary, EX stands for existing condition, DX stands for diagnosis, and TX stands for treatment. The existing condition (EX) may be a filling 280 (type of filling 290, 292, 294, 296), broken 284 half of tooth, or decay 282 on a certain spot on the tooth. The diagnosis (DX) may be, for example, a failing alloy 290 filling 280, open margins, or recurrent decay 282 on mesial 266. The recommended treatment (TX) may be, for example, a crown 298, gold 296 inlay 297, porcelain 294 inlay 297, or composite 292 filling 280. There will be the ability to choose different options of treatment (such as a root canal 234 on tooth #30 or a removal 252 of tooth #30) and treatment plan (for example, an implant 254).

When a user presses the probing chart key 221, the computer will automatically pull up the patient's periodontal chart.

On the right side of the device are the buttons 222, 224, 226, 228, 230 used for inputting information regarding the periodontal health of the tooth. The most common measurements are represented with buttons 222 representing millimeter readings of the periodontal pockets from 1 mm to 6 mm. The less common measurements are represented with smaller buttons 224 from 7 mm to 12 mm for each tooth. A bleeding point button 226 can be pressed for the mesial, middle reading, and distal readings. As an example, tooth #2 has a facial reading of 3-5-4, bleeding points on both mesial and middle readings, and class I mobility. The sequence of buttons that will be pressed will be #2 on the upper left of the device (to select tooth #2), the bleeding point button 226, probing buttons 3-5-4 (from buttons 222 and buttons 224), the mobility button 228, and one of the class buttons 230 designating mobility class I. This will give a very accurate reading of the existing periodontal condition of tooth #2.

Pressing the image capture button 232 and the computer pulls up the intraoral camera. The way pictures will be taken is that when the assistant, for example, presses #4 and the camera will be active and then points camera to tooth #4, the image will be stored in the patient's computer chart as tooth #4. That way, when data is pulled for tooth #4 there will be an existing condition of what the patient's tooth looked like when they first joined the practice, along with an image of the tooth, the periodontal health of the tooth, the proposed treatment was at the time, and the treatment that was rendered on the tooth.

An assistant, doctor, or hygienist can enter a full treatment plan on this keyboard 10 without having to use a mouse. Because using a mouse in the dental operatory is awkward, at best, and tends to really slow down the data entry, which causes the assistant to skip over pertinent data, this keyboard 10 improves the efficiency of the examination and also reduces data-entry errors.

The keyboard 10 includes specialized keys for typical examination procedures. Activating (or depressing) one of the specialized keys sends a data packet encoded to the computer 15, the data packet or string of information from the keyboard 10 is converted into conventional data as if entered via a mouse and graphical user interface or a conventional keyboard. The specialized key is essentially a "short-cut" or "hot key" that enables one keystroke to replace an entire sequence of keystrokes or mouse clicks.

Common treatments and the corresponding specialized keys include: RCT (root canal therapy) key 234; PFM (Porcelain Fused to Metal crown) key 236; FGC (Full Gold Crown) key 238; A.Prophy (Adult prophy) key 240; C.Prophy (Child Prophy) key 242; SRP (Scaling and Root Planning) key 244; Pontic (Middle fake tooth on a bridge) key 246; Part Denture key 248; and Full Denture (complete denture, no teeth on upper or lower arch) key 250, for example.

Additional specialized operations and corresponding keys on the specialized keyboard 10 or virtual keyboard 100 on a touch-screen include: an F (Facial or Buccal) key 260; an L (Lingual or Palatal, that is palate side or tongue side) key 262; a D (Distal, the back side of the tooth) key 264; an M (Mesial, the front side of the tooth) key 266; and an I/O (Incisal or Occlusal, the top side of the tooth or the chewing surface of the tooth—in the anterior teeth case that is called incisal) key 268. These five keys arrange in a cross pattern and are offset from other groupings of keys. The key layout is the standard layout of the shape of a tooth as depicted on the various dental software tools and this makes it effortless for the operator of the keyboard to enter the data on each tooth accurately and in a fast manner. Although the preferred embodiment, as illustrated in the appended drawing, describes a particular layout of keys thought to be advantageous in their layout for rapid data entry, other contemplated embodiments include additional keys, reduction of the number of keys, or rearrangement of the physical layout of keys to provide alternate layouts as ergonomics or other criteria may dictate.

Other specialized operations and corresponding keys on the specialized keyboard 10 or virtual keyboard 100 on a touch-screen include: FMX (Full Mouth Series of X-rays) key; BW (Bitewing X-ray) key 272; PA (Periapical X-ray) key 274; PANO (Panoramic X-ray) key 276; and Class V (filling a filling on the gum line of the tooth whether it is lingual or facial) key 280, for example. The FMX, full mouth series of X-rays corresponds to a full series of radiographs to be taken on a new patient's first visit. The BW key 272 for taking Bitewing X-rays, is used to see in between teeth.

The LCD display 200 displays the data entered and has a 2 second time lapse so that data can be reviewed prior to having it sent to the software, this way the person entering the data can intercept it and change it if he/she sees that they made a mistake in the data entry.

Using the keyboard of the present invention overcomes limitations in the existing art. Currently, a dentist must use a combination of a conventional keyboard and a mouse to select and input treatments, observed conditions, and current tooth condition (for example). The present invention, however, replaces the combination of screen, mouse, and conventional keyboard. Instead, the dentist rapidly uses the specialized keyboard of the present invention to capture a string of observations or treatment plans and observes the input on the small LCD screen 200 prior to "entering" the sequence into the host computer.

Other contemplated physical structures of the specialized keyboard are contemplated including a laser keyboard, such as an I-Tech Virtual Laser Keyboard available from Power Positioning Ltd. of Grawn, Mich., or a flat panel, or touch screen-type input device with reconfigurable keys based on a graphical user interface, or a membrane keyboard. Examples of membrane and touch screen input devices that could be adapted for use by the present invention include the devices manufactured by CSI Keyboards, Inc. of Peabody, Mass., USA, for example.

As mentioned above, one embodiment of the contemplated present invention includes adapting a keyboard for use on a touch-screen device and is shown in FIGS. 3-12. The above buttons and keys can be directly translated to virtual buttons and keys rendered on a touch-screen device, such as an IPAD® and the like, by means well known and understood in the art. The reader is encouraged to contemplate the aforementioned physical, mechanical keys and buttons as virtual keys on the display of common touch screen devices. Accordingly, a second preferred embodiment of the present invention contemplates use of the IPAD® (registered trademark of Apple, Inc. of San Jose, Calif., USA) or other similar tablet computers that include a touch-screen input/output device.

One particularly well-suited embodiment of the present invention contemplates a software application ("app") adapted for use on a tablet computer including the Apple IPAD® (available from www.apple.com) and other similar touch-screen interface tablet devices. In one preferred embodiment, the invention is ported for use on an IPAD® and details of this embodiment are described hereinafter, but should not be deemed limiting in scope because of the reference to a particular piece of hardware, but exemplary or representational of the spirit and scope of the present invention.

Digital X-ray images of a patient's teeth, jaw, and other related bone structure are common-place in today's dental office. Transferring the image from the digital X-ray recording device to a display associated with a personal computer is well-understood. Accordingly, transferring such an image to a touch screen device is readily feasible by those of ordinary skill in this art. The present invention contemplates using this image on the touch-screen and overlaying a graphical representation of a single tooth so that details of observed conditions may be displayed for use by the dentist and patient. Further, recommended treatment, past treatment and future conditions may also be graphically superimposed over the digital X-ray. Additionally, all the patient's teeth may be digitally X-rayed and a composite map of the patient's mouth using multiple X-ray images can be assembled so that all the teeth can be viewed simultaneously on the touch screen display. This also includes multiple views of each tooth and allows for graphical manipulation of each and every tooth in each and every view to demonstrate currently observed conditions of the teeth and/or to graphically display the proposed treatment options for any of the teeth.

In yet another contemplated embodiment, the present invention utilizes the camera resident on a handheld device (such as an IPAD®, IPHONE®, other smart phones, and other tablet computing devices, for example) to recognize gestures by the dentist. The gestures correspond to a predetermined set of instructions associated with a particular gesture or sequence of gestures, which can be hand gestures, or whole body gestures, to input commands or data in lieu of touching a keyboard or touch screen interface. Similarly, voice recognition input transferred to the smart appliance by the on-board microphone is also contemplated.

Additionally, the resident camera can be used to image the existing dental work inside a patient's mouth, and using imaging software, the type of dental work (bridge, crown, silver filing, ceramic filing, etc.) can be determined by the present invention and stored in a database and visually superimposed on an image on the screen of the device. For example, a "Cerac" machine that recognizes fillings, gold crowns, and silver filings can be integrated into the devices of the present invention.

Further, another embodiment of the present invention contemplates incorporating automated supply ordering and inventory control based on the procedure or treatment inputted by the dentist. This inventory control module/app, whereby the type of procedure selected launches a predetermined supply list and pulls the virtual inventory to verify if there is sufficient stock and automatically re-orders stock at set threshold points, and includes a payment set up similar to an "ITUNES®" online store, is automated in various embodiments of the present invention. Thus, when a dentist schedules a particular procedure for a given patient, the present invention then enables the dentist to view on a screen all the steps of that procedure and to customize the procedure for the patient by various on-screen pull down menus and/or by selecting or deselecting tick-boxes. Once the dentist is satisfied with the exact sequence and elections of a particular procedure (a unique procedure for that patient), the system will provide a list of needed supplies, which can be printed or otherwise delivered to the assistant for physical pulling of the supplies from their physical storage location. Simultaneously, the system of the present invention can pull virtual supplies from an inventory database and, if a predetermined re-order point is triggered, automatically send a re-order request to the vendors associated with those supplies. Billing and invoicing of the patient, and payment to vendors for supplies, can also be automated by well understood practices and devices known in the relevant arts.

The disclosure of the present invention herein includes selected terms, and the following shall serve as a partial definition of the meaning of these terms. The definitions include various examples and/or forms of components that fall within the scope of a particular term and can be used to implement the disclosed methods. The examples are not intended to be limiting and both singular and plural forms of terms may be within the definitions.

As used in this application, the term "computing unit" refers to a computer-related entity, hardware, firmware, software, a combination thereof, or software in execution. For example, a computing unit can be, but is not limited to being, a process running on a processor unit, a processor, an object, an executable, a thread of execution, a program, and a computer. By way of illustration, both an application running on a server and the server can be computing units. One or more computing units can reside within a process and/or thread of execution and a computing unit can be localized on one computer and/or distributed between two or more computers.

The term "system memory," as used herein, refers to a medium that participates directly or indirectly to provide signals, instructions, and/or data. A system memory may take forms, including, but not limited to, non-volatile media and volatile media. Non-volatile media may include, for example, optical or magnetic disks and so on. Volatile media may include, for example, optical or magnetic disks, dynamic memory and the like. Common forms of a system memory include computer-readable medium such as, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, and other media from which a computer, a processor or other electronic device can read.

The term "shared data storage," as used herein, refers to a physical and/or logical entity that can store data. Data storage may be, for example, a database, a table, a file, a list, a queue, a heap, a memory, a register, a file directory, a storage location, and so on. Data storage may reside in one logical and/or physical entity and/or may be distributed between two or more logical and/or physical entities.

The term "logic," as used herein, includes, but is not limited to, hardware, firmware, software and/or combinations of each to perform a function(s) or an action(s), and/or to cause and execute a function or action from another logic, method, and/or system. For example, based on a desired application or needs, logic may include a software controlled microprocessor, discrete logic like an application specific integrated circuit (ASIC), a programmed logic device like a field programmable gate array (FPGA), a memory device containing instructions, combinations of logic devices, or the like. Logic may include one or more gates, combinations of gates, or other circuit components. Logic may also be fully embodied as software, or may be a computing unit as defined herein. Where multiple logical logics are described, it may be possible to incorporate the multiple logical logics into one physical logic. Similarly, where a single logical logic is described, it may be possible to distribute that single logical logic between multiple physical logics.

The term "software," as used herein, includes, but is not limited to, one or more computer or processor instructions that can be read, interpreted, compiled, and/or executed, and that cause a computer, processor, or other electronic device to perform functions, actions, and/or behave in a desired manner. The instructions may be embodied in various forms like routines, algorithms, modules, methods, threads, and/or programs including separate applications or code from dynamically linked libraries. Software may also be implemented in a variety of executable and/or loadable forms including, but not limited to, a stand-alone program, a function call (local and/or remote), a servelet, an applet, instructions stored in a memory, part of an operating system, or other types of executable instructions. It will be appreciated by one of ordinary skill in the art that the form of software may be dependent on, for example, requirements of a desired application, the environment in which it runs, and/or the desires of a designer/programmer or the like. It will also be appreciated that computer-readable and/or executable instructions can be located in one logic and/or distributed between two or more communicating, co-operating, and/or parallel processing logics, and thus can be loaded and/or executed in serial, parallel, massively parallel, and other manners.

Suitable software for implementing the various components of the example systems and methods described herein include programming languages and tools like JAVA®, Pascal, C#, C++, C, CGI, PERL®, PHP, SQL, APis, SDKs, assembly, firmware, microcode, and/or other languages and tools. Software, whether an entire system or a component of a system, may be embodied as an article of manufacture and maintained or provided as part of a computer-readable memory as indicated previously. Another form of the software may include signals that transmit program code of the software to a recipient over a network or other communication medium. Thus, in one example, a computer-readable medium has a form of signals that represent the software/firmware as it is downloaded from a web server to a user. In another example, the computer-readable medium has a form of the software/firmware as it is maintained on the web server. Other forms may also be used.

The term "user," as used herein, includes, but is not limited to, one or more persons, software, computers, or other devices, or combinations of these.

The vendor may complete a sale in response to an acquisition or to a request after product demonstration. It will be appreciated by one of ordinary skill in the art that a vendor may take the form of a buyer, for example, in a supply chain, but a vendor is not limited to being a supplier. For all intents and purposes, a "vendor," as used herein, is a seller.

The term "buyer," as used herein, includes any person who contracts to acquire product in return for some form of consideration. The buyer may initiate a sale through a request for a particular product. It will be appreciated by one of ordinary skill in the art that a buyer may take the form of a customer.

"Consumer," as used herein, includes any person or entity that is capable of using the product sold. It will be appreciated by one of ordinary skill in the art that a consumer can be both a seller and a buyer depending on the type of sale.

Some portions of the detailed descriptions that follow are presented in terms of algorithms and symbolic representations of operations on data bits within a memory. These algorithmic descriptions and representations are the means used by those skilled in the art to convey the substance of their work to others. An algorithm is here, and generally, conceived to be a sequence of operations that produce a result. The operations may include physical manipulations of physical quantities. Usually, though not necessarily, the physical quantities take the form of electrical, audio, or magnetic signals capable of being stored, transferred, combined, compared, and otherwise manipulated in a logic and the like.

It has proven convenient at times, principally for reasons of common usage, to refer to these signals as bits, values, elements, symbols, characters, terms, numbers, or the like. It should be borne in mind, however, that these and similar terms are to be associated with the appropriate physical quantities and are merely convenient labels applied to these quantities. Unless specifically stated otherwise, it is appreciated that throughout the description, terms like defining, recording, importing, exporting, receiving, connecting, displaying, playing, or the like, refer to actions and processes of a computer system, logic, processor, or similar electronic device that manipulates and transforms data represented as physical (electronic) quantities.

Figure 13:
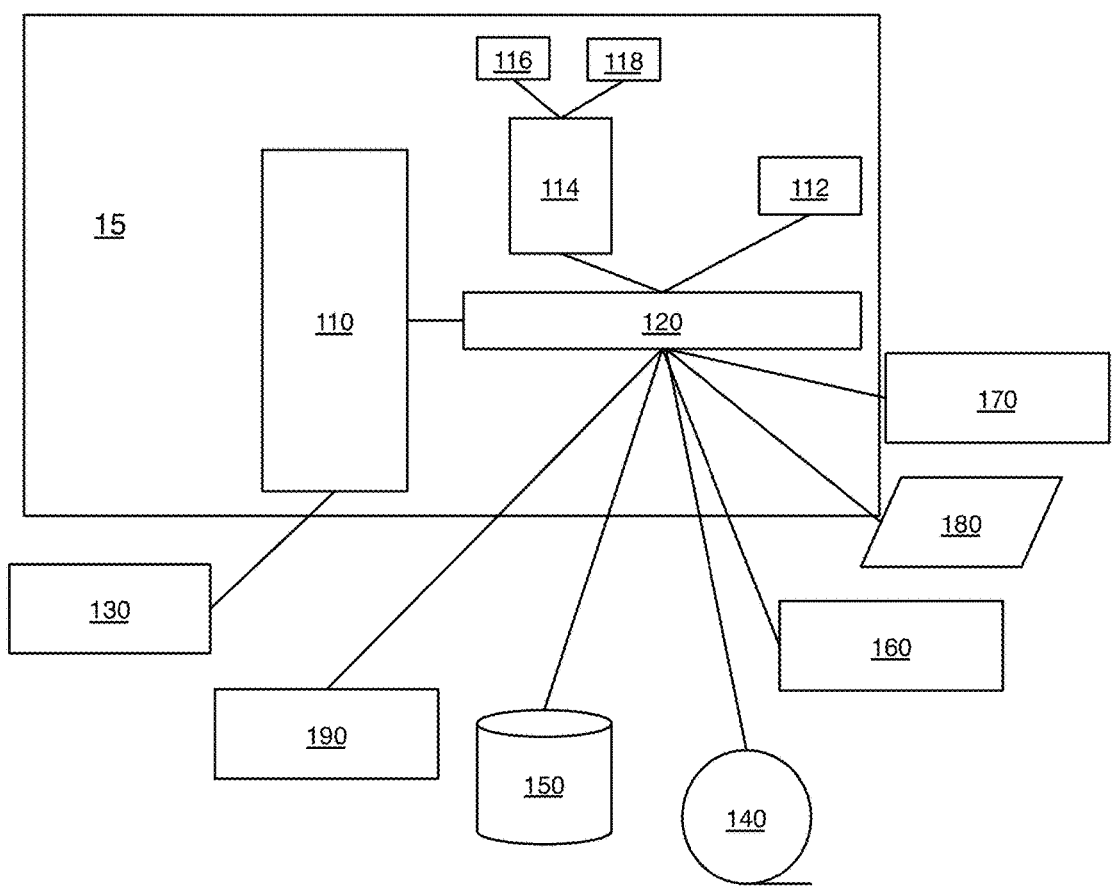
FIG. 13 is a schematic diagram of a computer system utilizing the device and system and method according to a preferred embodiment of the present invention.

Referring to the drawings, wherein like reference numerals represent like parts throughout the various drawing figures, FIG. 13 shows a schematic view of a programmable computing device 15.

Various examples of the present invention may be implemented using electronic circuitry (not shown) configured to perform one or more functions. For example, with some embodiments of the invention, the online method may be implemented using one or more ASICs. More typically, however, components of various examples of the invention will be implemented using a programmable computing device or computer 15 executing firmware or software instructions, or by some combination of purpose-specific electronic circuitry and firmware or software instructions executing on a programmable computing device or computer 15.

Accordingly, FIG. 1 and FIG. 13 show one illustrative example of a computer 15 that can be used to implement various embodiments of the invention. The computer 15 may be incorporated within a variety of consumer electronic devices, such as personal media players, cellular phones, smart phones, personal data assistants, global positioning system devices, and the like.

As seen in FIG. 13, computer 15 has a computing unit 110. Computing unit 110 typically includes a processor or processing unit 112 and a system memory 114. Processing unit 112 may be any type of processing device for executing software instructions, but will conventionally be a microprocessor device. System memory 114 may include both a read-only memory (ROM) 116 and a random access memory (RAM) 118. As will be appreciated by those of ordinary skill in the art, both read-only memory (ROM) 116 and random access memory (RAM) 118 may store software instructions to be executed by processing unit 112.

Processing unit 112 and system memory 114 are connected, either directly or indirectly, through a bus 120 or alternate communication structure to one or more peripheral devices. For example, processing unit 112 or system memory 114 may be directly or indirectly connected to additional memory storage, such as a removable magnetic disk drive 140, a hard disk drive 150, a flash memory card 160, and a removable optical disk drive 170. Processing unit 112 and system memory 114 also may be directly or indirectly connected to one or more input devices 180 and one or more output devices 190. Input devices 180 may include, for example, a keyboard, touch-screen, a remote control pad, a pointing device (such as a mouse, touchpad, stylus, trackball, or joystick), a scanner, a camera, or a microphone. Output devices 190 may include, for example, a monitor display, an integrated display, television, printer, stereo, or speakers.

Still further, computing unit 110 will be directly or indirectly connected to one or more network interfaces 130 for communicating with a network. This type of network interface 130, also sometimes referred to as a network adapter or network interface card (NIC), translates data and control signals from computing unit 110 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device 15 may be connected to a variety of other peripheral devices, including some that may perform input, output, and storage functions, or some combination thereof. For example, the computer 15 may be connected to handheld devices including an IPAD®, tablet computers, or other similar portable devices.

The computer 15 may be connected to or otherwise include one or more other peripheral devices, such as a telephone (not shown). The telephone may be, for example, a wireless "smart phone," such as IPHONE® or DROID®-brand smart phones. As known in the art, this type of telephone communicates through a wireless network using radio frequency transmissions. In addition to simple communication functionality, a "smart phone" may also provide a user with one or more data management functions, such as sending, receiving, and viewing electronic messages (e.g., electronic mail messages, SMS text messages, etc.), recording or playing back sound files, recording or playing back image files (e.g., still picture or moving video image files), viewing and editing files with text (e.g., MICROSOFT® Word or EXCEL® files, or ADOBE® ACROBAT® files), etc. Because of the data management capability of this type of telephone, a user may connect the telephone with computer 15 so that their data maintained may be synchronized.

Of course, still other peripheral devices may be included with or otherwise connected to a computer 15 of the type illustrated in FIG. 13, as is well known in the art. In some cases, a peripheral device may be permanently or semi-permanently connected to computing unit 110. For example, with many computers, a computing unit 110, a hard disk drive 150, a removable optical disk drive 170, and a display (not shown) are semi-permanently encased in a single housing.

Still other peripheral devices may be operably communicating with, and removably connected to the computer 100. Computer 15 may include, for example, one or more communication ports (not shown) through which a peripheral device can be connected to computing unit 110 (either directly or indirectly through bus 120). These communication ports may thus include a parallel bus port or a serial bus port, such as a serial bus port using the Universal Serial Bus (USB) standard or the IEEE 1394 High Speed Serial Bus standard (e.g., a FIREWIRE® port). Alternately or additionally, computer 15 may include a wireless data "port," such as a BLUETOOTH® interface, a WI-FI® interface, an infrared data port, or the like.

It should be appreciated that a computing device 15 may include more components than computer 15 illustrated in FIG. 13, fewer components than computer 15, or a different combination of components than computer 15. Some implementations of the invention, for example, may employ one or more computing devices 15 that are intended to have a very specific functionality, such as a smart phone or server computer. These computing devices may thus omit unnecessary peripherals, such as the network interface 130, removable optical disk drive 140, printers, scanners, external hard drives, etc. Some implementations of the invention may alternately or additionally employ computing devices 15 that are intended to be capable of a wide variety of functions, such as a desktop or laptop personal computer. These computing devices 15 may have any combination of peripheral devices or additional components as desired.

In the flow diagrams, blocks denote "processing blocks" that may be implemented with logic. In the case where the logic may be software, a flow diagram does not depict syntax for any particular programming language, methodology, or style (e.g., procedural, object-oriented). Rather, a flow diagram illustrates functional information one skilled in the art may employ to develop logic to perform the illustrated processing. It will be appreciated that in some examples, program elements like temporary variables, routine loops, and so on are not shown. It will be further appreciated that electronic and software logic may involve dynamic and flexible processes so that the illustrated blocks can be performed in other sequences that are different from those shown and/or that blocks may be combined or separated into multiple components. It will be appreciated that the processes may be implemented using various programming approaches like machine language, procedural, object oriented, and/or artificial intelligence techniques. The foregoing applies to all methodologies herein.

Although the invention has been particularly shown and described with reference to certain embodiments, it will be understood by those skilled in the art that various changes in form and detail may be made without departing from the spirit and scope of the invention.

I claim:

1. A dental examination system for use with a dental examination software tool, the dental examination software tool being able to record conditions of a patient's teeth and store the records in an associated patient's computer chart of the dental examination software tool, the system comprising:
   (a) a host computer having a central processor, at least one output screen or monitor device, and at least one input device, the dental examination software tool resident on the host computer;
   (b) a specialized dental keyboard/input-output device having a plurality of input keys, said specialized dental keyboard/input-output device physically distinct from said host computer;
   (c) each input key having an associated data string recognizable by the dental examination software tool; and
   (d) groupings of input keys specific to dental procedures, wherein each grouping includes a plurality of said input keys, the distance between adjacent input keys of the grouping being smaller than the distance between the input keys of the grouping and input keys not associated with the grouping, comprising:
       (i) a tooth surface grouping of input keys comprising:
           an I/O (Incisal or Occlusal, the top side of the tooth or the chewing surface of the tooth in the anterior teeth case that is called incisal) input key;
           an M (Mesial, the front side of the tooth) input key;
           a D (Distal, the back side of the tooth) input key;
           an L (Lingual or Palatal, that is palate side or tongue side) input key; and
           an F (Facial or Buccal) input key;
           wherein the I/O input key is centrally positioned, the M input key is positioned above the I/O input key, the D input key is positioned below the I/O input key, the L input key is positioned to the left of the I/O input key, and the F input key is positioned to the right of the I/O input key, such that the I/O input key, the M input key, the D input key, the L input key, and the F input key are arranged in a cross pattern; and
       (ii) a tooth grouping of tooth input keys, each tooth input key designating a specific tooth, consisting of:
           a first set and a second set of tooth input keys, the first set and the second set each having 16 or 17 tooth input keys, the first set being consecutively numbered representing the correspondingly numbered teeth of the upper arch of a mouth, and the second set being reverse consecutively numbered representing the correspondingly numbered teeth of the lower arch of a mouth.

2. The system of claim 1, the specialized dental keyboard/input-output device further comprising an image capture button, the image capture button for activating a camera to create an image, the image being stored in the associated patient's computer chart of the dental examination software tool, the camera being an intra-oral camera.

3. The system of claim 1, the specialized dental keyboard/input-output device further comprising an image capture button, the image capture button for activating a camera to provide input images of human gestures, a pre-determined set of command or data instructions being associated with particular individual gestures or particular sequences of gestures, recognized input images of human gestures activating the command or data instructions to implement commands or input data.

4. The system of claim 1, further comprising a periodontal grouping of a plurality of periodontal input keys, the periodontal grouping comprising:
   (a) a first set of the most common periodontal input keys; and
   (b) a second set of less common periodontal input keys.

5. The system of claim 1, further comprising an examination grouping a plurality of examination input keys, the examination grouping comprising:
   (a) an EX examination input key for indicating the current condition of the tooth;
   (b) a DX examination input key for indicating the diagnosis of the tooth; and
   (c) a TX examination input key for indicating the prescribed treatment of the tooth.

6. The system of claim 1, wherein said first set of at least 16 tooth input keys of said tooth surface grouping of input keys further includes an additional permanent teeth input key.

7. The system of claim 1, wherein said second set of at least 16 tooth input keys of said tooth surface grouping of input keys further includes an additional primary teeth input key.

8. The system of claim 1, the plurality of input keys further comprising at least three input keys selected from the group of input keys consisting of:
   (a) an RCT (Root Canal Therapy) key;
   (b) a PFM (Porcelain Fused to Metal crown) key;
   (c) an FGC (Full Gold Crown) key;
   (d) an A.Prophy (Adult Prophy) key;
   (e) a C.Prophy (Child Prophy) key;
   (f) an SRP (Scaling and Root Planing) key;
   (g) a Pontic (middle fake tooth on a bridge) key;
   (h) a Part Denture (partial denture) key; and
   (i) a Full Denture (complete denture, no teeth on upper or lower arch).

9. The system of claim 1, further comprising an integrated display panel for displaying a sequence of keystrokes.

10. The system of claim 1, wherein specialized dental keyboard/input-output device is a flat panel or touch-screen-type input device, and the plurality of input keys are reconfigurable input keys of a graphical user interface.

11. The system of claim 1, wherein each grouping of keys is set apart from other keys that are not associated with the grouping.

12. The system of claim 1, wherein keys that are not associated with the grouping are not positioned between keys of a grouping.

13. The system of claim 1, wherein said first set of at least 16 tooth input keys is above and adjacent to said second set of at least 16 tooth input keys.

14. The system of claim 1, wherein said first set of at least 16 tooth input keys is directly above said second set of at least 16 tooth input keys.

15. A specialized dental keyboard/input-output device adapted for recording conditions of teeth in a patient during a dental exam using a dental examination software tool, the specialized dental keyboard/input-output device comprising:
   (a) a display area;
   (b) groupings of input keys specific to dental procedures, wherein each grouping includes a plurality of said input keys, the distance between adjacent input keys of the grouping being smaller than the distance between the input keys of the grouping and input keys not associated with the grouping, comprising:
(i) a tooth surface grouping of input keys comprising:
an I/O (Incisal or Occlusal, the top side of the tooth or the chewing surface of the tooth—in the anterior teeth case that is called incisal) input key;
an M (Mesial, the front side of the tooth) input key;
a D (Distal, the back side of the tooth) input key;
an L (Lingual or Palatal, that is palate side or tongue side) input key; and—an F (Facial or Buccal) input key;
wherein the I/O input key is centrally positioned, the M input key is positioned above the I/O input key, the D input key is positioned below the I/O input key, the L input key is positioned to the left of the I/O input key, and the F input key is positioned to the right of the I/O input key, such that the I/O input key, the M input key, the D input key, the L input key, and the F input key are arranged in a cross pattern; and
(ii) a tooth grouping of tooth input keys, each tooth input key designating a specific tooth, consisting of:
a first set and a second set of tooth input keys, the first set and the second set each having 16 or 17 tooth input keys, the first set being consecutively numbered representing the correspondingly numbered teeth of the upper arch of a mouth, and the second set being reverse consecutively numbered representing the correspondingly numbered teeth of the lower arch of a mouth.

16. The specialized dental keyboard/input-output device of claim 15, the dental examination software tool resident on a host computer, the specialized dental keyboard/input-output device physically distinct from said host computer and adapted for use with the host computer, the dental keyboard/input-output device adapted to communicate bi-directionally with the dental examination software tool resident on a host computer, the host computer having a central processor, at least one output screen or monitor device, and at least one input device.

17. The specialized dental keyboard/input-output device of claim 15, the dental examination software tool resident on a host computer, the host computer having a central processor, at least one output screen or monitor device, and at least one input device, wherein the specialized dental keyboard/input-output device is physically distinct from said host computer and adapted for use with the host computer, the dental keyboard/input-output device further comprising:
(a) a wired or wireless connection coupled to the host computer for sending inputted data representing a plurality of keystrokes; and
(b) a set of programming sequences resident on the host computer adapted to convert inputted keystrokes to a data string recognizable by the dental examination software tool.

18. The specialized dental keyboard/input-output device of claim 15 wherein one of the plurality of input keys is an image capture button.

19. The specialized dental keyboard/input-output device of claim 15 wherein one of the plurality of input keys is an image capture button for activating a camera, the camera in data communication with the dental examination software tool, and the camera is configured to image dental work inside a patient's mouth.

20. The specialized dental keyboard/input-output device of claim 15 wherein one of the plurality of input keys is an image capture button for activating a camera, the camera in data communication with the dental examination software tool, and the camera is configured to recognize at least one pre-determined gesture as an input to at least one input key.

21. The specialized dental keyboard/input-output device of claim 15, further comprising a periodontal grouping of a plurality of periodontal input keys, the periodontal grouping comprising:
(a) a first set of the most common periodontal input keys; and
(b) a second set of less common periodontal input keys.

22. The specialized dental keyboard/input-output device of claim 15, further comprising an examination grouping a plurality of examination input keys, the examination grouping comprising:
(a) an EX examination input key for indicating the current condition of the tooth;
(b) a DX examination input key for indicating the diagnosis of the tooth; and
(c) a TX examination input key for indicating the prescribed treatment of the tooth.

23. The specialized dental keyboard/input-output device of claim 15, wherein said first set of at least 16 tooth input keys of said tooth surface grouping of input keys further includes an additional permanent teeth input key.

24. The specialized dental keyboard/input-output device of claim 15, wherein said second set of at least 16 tooth input keys of said tooth surface grouping of input keys further includes an additional primary teeth input key.

25. The specialized dental keyboard/input-output device of claim 15, the plurality of input keys further comprising at least three input keys selected from the group of input keys consisting of:
(a) an RCT (Root Canal Therapy) key;
(b) a PFM (Porcelain Fused to Metal crown) key;
(c) an FGC (Full Gold Crown) key;
(d) an A.Prophy (Adult Prophy) key;
(e) a C.Prophy (Child Prophy) key;
(f) an SRP (Scaling and Root Planing) key;
(g) a Pontic (middle fake tooth on a bridge) key;
(h) a Part Denture (partial denture) key; and
(i) a Full Denture (complete denture, no teeth on upper or lower arch).

26. The specialized dental keyboard/input-output device of claim 15, wherein the display area is an integrated display panel for displaying a sequence of keystrokes.

27. The specialized dental keyboard/input-output device of claim 15, wherein specialized dental keyboard/input-output device is a flat panel or touch-screen-type input device, and the plurality of input keys are reconfigurable input keys of a graphical user interface.

28. The specialized dental keyboard/input-output device of claim 15, wherein each grouping of keys is set apart from other keys that are not associated with the grouping.

29. The specialized dental keyboard/input-output device of claim 15, wherein keys that are not associated with the grouping are not positioned between keys of a grouping.

30. The specialized dental keyboard/input-output device of claim 15, wherein said first set of at least 16 tooth input keys is above and adjacent to said second set of at least 16 tooth input keys.

31. The specialized dental keyboard/input-output device of claim 15, wherein said first set of at least 16 tooth input keys is directly above said second set of at least 16 tooth input keys.

* * * * *